United States Patent [19]
Crawford

[11] Patent Number: 5,827,248
[45] Date of Patent: Oct. 27, 1998

[54] MENSTRUAL CUP

[75] Inventor: Lou H. Crawford, Cincinnati, Ohio

[73] Assignee: The Keeper Co., Inc., Cincinnati, Ohio

[21] Appl. No.: 154,344

[22] Filed: Nov. 18, 1993

[51] Int. Cl.[6] .......................................................... A61F 5/44
[52] U.S. Cl. ............................................. 604/328; 604/329
[58] Field of Search ..................................... 128/837–841; 604/327–330, 335; 251/4, 342

[56] References Cited

U.S. PATENT DOCUMENTS

| | | | |
|---|---|---|---|
| 274,447 | 3/1883 | Kennish | ................................... 251/342 |
| D. 323,212 | 1/1992 | Crawford . | |
| 1,891,761 | 12/1932 | Goddard . | |
| 2,089,113 | 8/1937 | Chalmers . | |
| 2,755,060 | 7/1956 | Twyman | ................................... 251/342 |
| 3,404,682 | 10/1968 | Waldron . | |
| 4,381,771 | 5/1983 | Gabbay | ................................... 128/837 |

FOREIGN PATENT DOCUMENTS

| | | | |
|---|---|---|---|
| 363939 | 11/1922 | Germany | ............................... 128/858 |

OTHER PUBLICATIONS

The Keeper, Inc., The Keeper™ Brochure, 1989, 1 page.
Nancy Friedman, "Everything You Mustn Know About Tampons", Berkley Book, pp. 140–145.

*Primary Examiner*—Mark O. Polutta
*Attorney, Agent, or Firm*—Frost & Jacobs LLP

[57] ABSTRACT

A catamenial device in the form of a menstrual cup. The menstrual cup is an integral one-piece structure formed of soft, resilient, fluid-proof material. The menstrual cup comprises a hollow body having open upper and lower ends. The body is symmetrical about its long axis, is of circular transverse cross-section throughout its length, and is approximately parabolic in cross section taken along a plane in which its long axis lies. The body, adjacent its open upper end has an external, outwardly extending, annular, rim arrangement adapted to engage the vaginal wall to prevent by-pass leakage. The device has a plurality of small pressure equalizing perforations formed in and evenly spaced about the body adjacent the rim arrangement. A tubular withdrawal extension projects from the lower end of the body and is substantially coaxial therewith. The withdrawal extension has a closable drainage passage therethrough communicating with the open lower end of the body.

14 Claims, 2 Drawing Sheets

MENSTRUAL CUP

TECHNICAL FIELD

The invention relates to a menstrual cup, and more particularly to a menstrual cup provided with a tubular withdrawal extention having a reclosable passage through which the menstrual cup can be drained without removal from the vagina.

BACKGROUND ART

Prior art workers have devised numerous types of catamenial devices. Of the various catamenial devices developed, the tampon and the napkin are the ones most commonly used today. While each of these devices serves its purpose well, both are characterized by certain drawbacks.

From an environmental standpoint, both tampons and napkins tend to clog plumbing and adversely affect water treatment plants. The plastic applicators associated with many tampons are non-biodegradable and are, in fact, substantially indestructible. The significance of this can be appreciated when it is understood that the annual sales of tampons in the United States, alone, are in the billions. Many applicators are characterized by sharp cusps and have been known to lacerate vaginal membranes. Instances are known where tampons have induced vaginal or cervical ulceration, or have fallen apart inside the vagina, leaving behind fibers that induce infections. The tampon withdrawal string can locate in the perineal region and is capable of wicking bacteria therefrom into the vagina. Napkins bridge the entire perineal area and can be breeding grounds for bacteria therefrom. Napkins can also be characterized by chafing and odor problems.

In recent years, there has been a renewed interest in the use of the menstrual cup. This is true for a number of reasons. First of all, the cost is far less than the use of tampons or napkins. Convenience and availability constitute additional factors. Since the menstrual cup is re-usable, only one is required per person. The useful life of a menstrual cup is at least about ten years or more. The use of a menstrual cup is odorless and non-polluting. Finally, the menstrual cup can be used to hold medication for the treatment of vaginal infections.

The present invention is directed to the improvement of catamenial devices of the menstrual cup type. As is well know to one skilled in the art, removal of the menstrual cup from the vagina should be accomplished on a regular basis for emptying, cleaning and hygenic purposes. It has been determined, however, that between such removal operations, it would be a matter of great convenience if the menstrual cup could be drained while in place. The present invention is based on the discovery that the withdrawal extension, if properly modified, may be used for this purpose. The withdrawal extension is provided in tubular form, having a longitudinal passage which communicates with the interior of the menstrual cup body. Means are provided to close the passage in the withdrawal extension and the withdrawal extension passage is normally kept closed. The closure means are of such nature, however, that with appropriate manipulation by the user, the passage may be opened for drainage purposes and thereafter reclosed.

DISCLOSURE OF THE INVENTION

According to the invention there is provided a catamenial device in the form of a menstrual cup. The menstrual cup constitutes an integral one-piece structure. The cup is formed of soft, resilient, fluid-proof material suitable for internal use in the body. The cup lends itself well to be molded of an appropriate rubber or plastic material.

The catamenial device of the present invention comprises a hollow, cup-like body having an open upper end. The body is symmetrical about its long axis and is of circular transverse cross-section throughout its length. The body is approximately parabolic in cross section taken along a plane in which its long axis lies.

At its lower end, he body terminates in an extension. The extension is of such length that it can be manually grasped for removal of the menstrual cup from the vagina. The menstrual cup body, adjacent the open upper end thereof, is provided with an annular rim arrangement adapted to engage the vaginal wall to greatly reduce or preclude by-pass leakage. A plurality of very small perforations are formed in the body, adjacent the rim arrangement, to facilitate removal of the menstrual cup from the vagina by precluding the formation of a vacuum within the vagina during the removal procedure.

The withdrawal extension is tubular in form, having a longitudinal passage formed therein throughout its length. The passage communicates with the interior of the menstrual cup body. Closure means are provided for the extension passage. The closure means are openable by the user for drainage purposes and thereafter are recloseable.

DETAILED DESCRIPTION OF THE INVENTION

Figure 1:
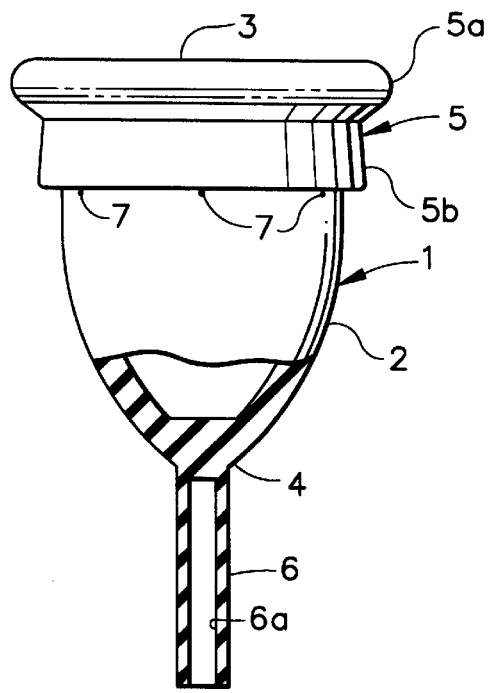
FIG. 1 is an elevational view, partly in cross section, of an exemplary prior art menstrual cup.

Reference is first made to FIG. 1 wherein an exemplary prior art menstrual cup is illustrated. The menstrual cup of FIG. 1 is generally indicated at 1 and comprises an integral, one-piece element. The menstrual cup 1 has a body 2 of the general shape of a parabaloid. The body 2 has an open end 3 and a closed end 4, being generally cup-shaped and hollow, as shown in FIG. 1.

The menstrual cup 1 lends itself well to being molded soft, resilient, fluid-proof material, suitable for internal use. Food grade gum rubber, for example, is frequently used for this purpose.

Near its open end 3, the menstrual cup 1 is provided with an exterior annular rim, generally indicated at 5. The rim 5 is of markedly increased thickness. The rim 5 has a rounded portion 5a leading to an outwardly flared skirt-like portion 5b. The rim 5 serves a number of purposes. First of all, it is the primary portion of the menstrual cup which is engaged by the vaginal walls to maintain the menstrual cup in its proper position. Secondly, it assures that the menstrual cup assumes its proper configuration after having been folded lengthwise upon itself for insertion in the vagina. Furthermore, it prevents by-pass leakage. Rim or rib arrangements, other than the one shown in the drawings herein, are well known in the art. The precise nature of the rim or rib arrangement is not a limitation of the present invention.

Figure 5:
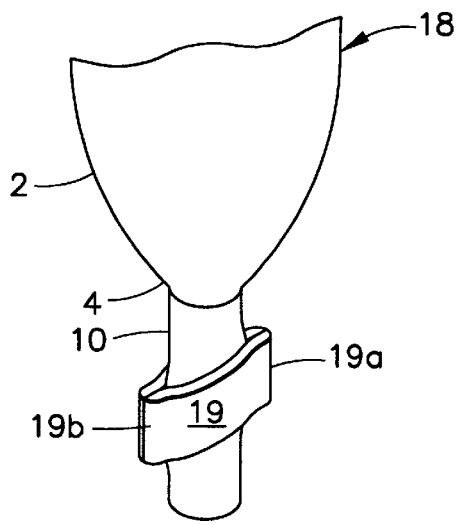
FIG. 5 is a fragmentary perspective view showing the tubular extension provided with a clip closure.

At its closed end 4, the menstrual cup 1 has a rod-like or tube-like extension 6. The extension 6 is of such length that it can be easily and conveniently manually grasped for removal of the menstrual cup 1 from the vagina. The extension 6 is preferably hollow and tubular as shown in FIG. 5 not only for molding considerations and material savings, but also to make the extension more pliable as a matter of comfort.

The menstrual cup 1 is completed by providing the body 2 with a plurality of tiny holes 7, evenly spaced about the body periphery. The holes 7 are located adjacent the skirt 5b and are of such size as to discourage fluid leakage therethrough. The holes 7 constitute pressure-relief holes precluding the formation of a vacuum within the vagina during removal of the menstrual cup 1.

Figure 2:
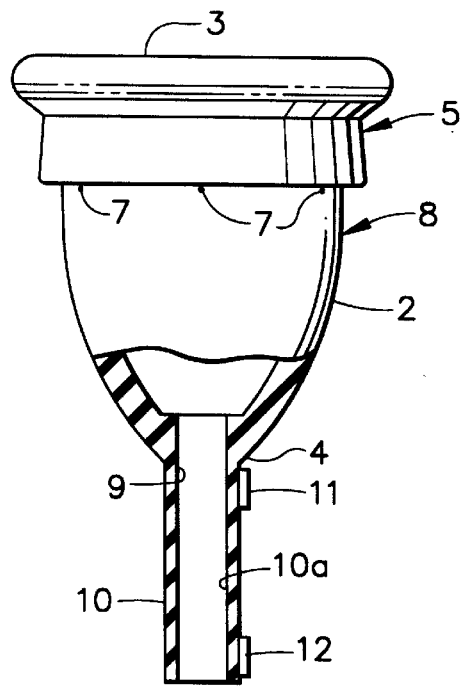
FIG. 2 is an elevational view, partly in cross section, of a menstrual cup according to the present invention.
Figure 3:
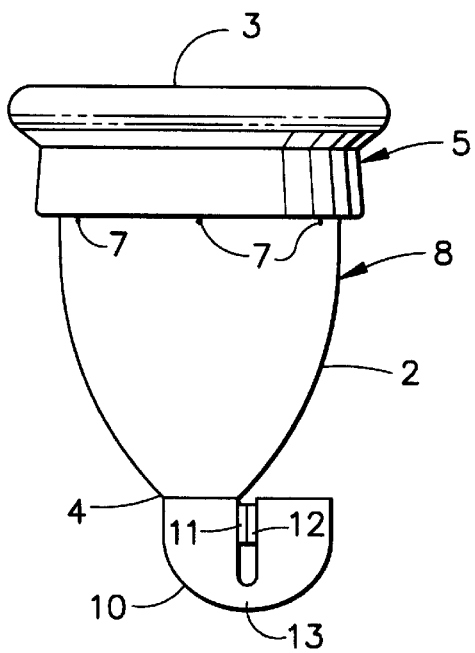
FIG. 3 is an elevational view of the menstrual cup of FIG. 2, illustrating the withdrawal extension in its closed position.

Reference is now made to FIGS. 2 and 3. In these Figures, the menstrual cup of the present invention is generally indicated at 8. The menstrual cup 8 of FIGS. 2 and 3 is similar in many respects to the prior art menstrual cup of FIG. 1. As a consequence, like parts have been given like index numerals. To this end, the menstrual cup 8 has a body 2 with an upper end 3, which is open, and a lower end 4. Adjacent the upper end, the menstrual cup 2 is provided with a rim arrangement generally indicated at 5. For purposes of an exemplary showing, the rim arrangement 5 of FIG. 2 is shown as being the same as the rim arrangement 5 of FIG. 1, although any appropriate rim or rib arrangement may be used. The body 2 may also be provided with a plurality of perforations 7, as in the case of the prior art embodiment of FIG. 1.

The embodiment of FIG. 2 differs from that of FIG. 1 in several important ways. First of all, it will be apparent that the lower end 4 of the body 2 of menstrual cup 8 is open, as at 9.

The body 2 of the menstrual cup 8 is provided with an integral downwardly directed extension 10. The extension 10 is similar to the extension 6 of FIG. 1 and is intended to serve the same withdrawal purpose. It will be noted, however, that the extension 10 has a larger external diameter and is provided with an internal passage 10a of larger diameter than the passage 6a of extension 6 of FIG. 1. It will further be noted that the passage 10a of extension 10 extends throughout the length thereof. The passage 10a at the upper end of extension 10 communicates with the opening 9 in the lower end 4 of body 2. The passage 10a also extends through the lower end of extension 10.

It will be apparent to one skilled in the art that if the menstrual cup 8 were mounted in the vagina, and if the extension 10 were in its open condition as shown in FIG. 2, fluid within the menstrual cup 8 would drain, without having to remove the menstrual cup 8 from the vagina. When in normal use, means must be provided to close the passage 10a so that the menstrual cup 8 can perform its purpose. Any appropriate means to close the passage 10a may be employed. The closure means must have a number of characteristics. First of all, the closure means must be easily manipulated by the user between its open and closed conditions. It must be reliable and leak proof. Finally, it must be comfortable and non-irritating.

In the embodiment of FIG. 2, a first piece of hook and loop type tape 11 is affixed to the extension 10 near its upper end. A second piece of hook and loop-type tape is affixed to the extension 10 near its lower end and is aligned with the tape 11. One of the tapes 11 and 12 is of the hook type, while the other is of the loop type so that the tapes 11 and 12 can coact. The tape segments 11 and 12 are affixed to the extension 10 in any appropriate manner including adhesively. To close the passage 10a of extension 10, so that the menstrual cup 8 can be used for its designed purpose, it is only necessary to fold extension 10 upon itself, causing tape segments 11 and 12 to interengage. This is illustrated in somewhat exaggerated form in FIG. 3, for purposes of clarity. At the point 13 where the extension 13 is folded, the passage 10a of the extension will be closed. To open passage 10a for purposes of drainage, it is only necessary to disengage tape segment 12 from tape segment 11. The extension 10 will immediately assume its normal position, and the passage 10a therethrough will be open, permitting fluid in the menstrual cup body 2 to drain therethrough.

Figure 4:
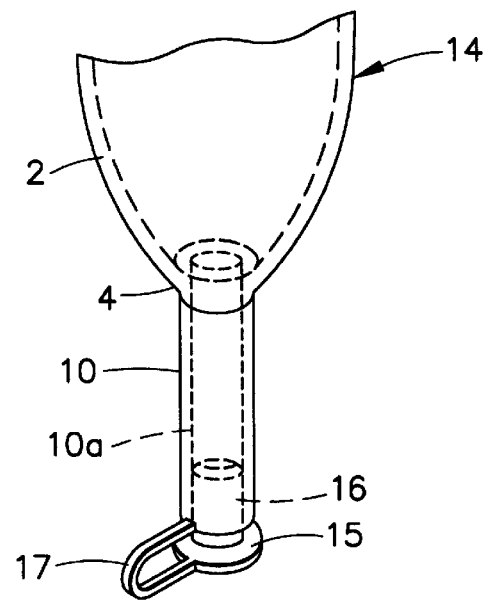
FIG. 4 is a fragmentary perspective view of a menstrual cup of the present invention wherein the tubular withdrawal extension is provided with a captive plug.

FIG. 4 illustrates another closure for the passage 10a of extension 10. The embodiment of FIG. 4 is generally indicated at 14 and differs from the embodiment of FIGS. 2 and 3 only with respect to the means used to close the passage 10a of extension 10. Again, like parts have been given like index numerals. In this instance, the passage 10a of extension 10 is closed by means of a small plug 15. The plug 15 has a portion 16 capable of being sealingly engaged in passage 10a. While not required, it is preferable that the plug 15 be captive with respect to the menstrual cup 14. This may be accomplished by means of a narrow filament 17 connected at one end to the lower end of extension 10 and at its other end to the plug 15. It will be understood by one skilled in the art that the entire menstrual cup assembly 14, including the filament 17 and plug 15 may comprise and integral, one-piece molded structure. Removal of the plug 15 from the passage 10a will open the passage, allowing fluid to drain from the menstrual cup body 2. When the draining operation in complete the plug 15 is simply reinserted in the passage 10a, and the menstrual cup 14 is ready for continued use.

Reference is now made to FIG. 5. The menstrual cup embodiment of FIG. 5, generally indicated at 18, is similar to those previously described with respect to FIGS. 2, 3 and 4. In this instance, the passage through withdrawal extension 10 is normally maintained closed by a spring clip 19 illustrated in its normal, passage-closing condition. Clip 19 may be made of resilient plastic or metal. If metal, it is preferably coated with a soft plastic layer. While not required, the clip 19 is preferably affixed to the withdrawal extension by adhesive means or the like. When the user grasps the ends 19a and 19b of clip 19 and squeezes them toward each other, the sides of the clip will bulge outwardly opening the passage in extension 10 for purposes of drainage. Upon release of the ends 19a and 19b of clip 19, it will return to its normal condition shown in FIG. 5, closing the passage 10a in extension 10.

The menstrual cup of embodiment 20 in FIG. 6 is again similar to the menstrual cups of FIGS. 2–5, and like parts have been given like index numerals. In this embodiment, the extension 10 is a tubular extension and has a cylindrical passage 10a wherein the cylindrical passage 10a, however, terminates short of the lower end of extension 10. The lower end 21 of extension 10 is flattened and solid. In this lower end 21 a slit 22 is formed, extending from the lowermost end of extension 10 to and communicating with the passage 10a. The slit 22 is configured to be normally closed. However, if the ends 21a and 21b of the flattened portion 21 are grasped by the user and squeezed toward each other (much in the fashion described with respect to clip 19 of FIG. 5), the slit 22 will open, allowing drainage of menstrual cup 20. Upon release of the ends 21a and 21b, the flattened portion 21 will return to its normal condition, and the slit 22 formed therein will reclose, enabling the menstrual cup to serve its purpose.

Figure 6:
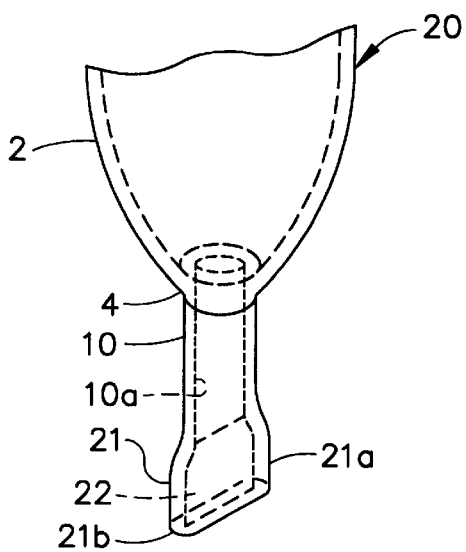
FIG. 6 is a fragmentary perspective view illustrating a menstrual cup having a tubular withdrawal extension the end of which is formed to be normally closed.
Figure 7:
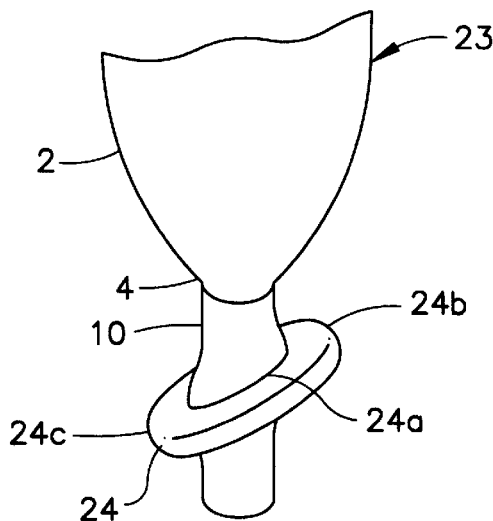
FIG. 7 is a fragmentary perspective view illustrating a menstrual cup having a tubular withdrawal extension normally closed by a soft plastic ring like member.
Figure 8:
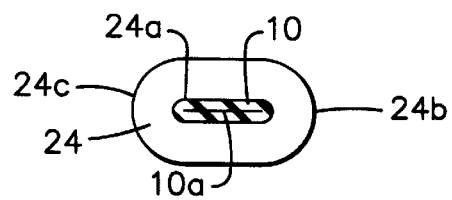
FIG. 8 is a cross sectional view through the extension of FIG. 7, illustrating the extension closed by the ring.

Another exemplary embodiment of the present invention is illustrated in FIGS. 7 and 8. The menstrual cup is generally indicated at 23. The menstrual cup 23 may be similar in configuration to those illustrated in FIGS. 2–6, and like parts have been given like index numerals. The extension 10 is similar to those illustrated in FIGS. 2, 4 and 5, being tubular and having a passage 10a (see FIG. 8) leading to the interior of the menstrual cup body 2. The passage 10a of the withdrawal extension 10 is normally closed by means of a clamp device 24. The clamp device 24 is made of resilient plastic or rubber and, as will be noted from FIG. 7, all of its peripheral edges are rounded. The clamp device 24 may have any appropriate peripheral configuration. For example, it may be oval, or obround as shown in the Figures. The closure device 24 has a central opening 24a so sized as to permit the extension 10 to pass therethrough only if sealingly collapsed upon itself as shown in FIG. 8. In this manner, the closure member 24 maintains the extension passage 10a normally closed. If the user grasps the ends 24b and 24c of closure device 24, and squeezes them toward each other (as described with respect to the clip 19 of FIG. 5 or the flattened portion 21 of FIG. 6), the opening 24a of the closure device will distort transversely, permitting the passage 10a to open and enabling the drainage of fluid from the body 2 of menstrual cup 23. Upon release of the ends 24b and 24c by the user, the resilient closure member 24 will again assume the shape shown in FIG. 8, closing the passage 10a in a fluid tight manner.

Figure 9:
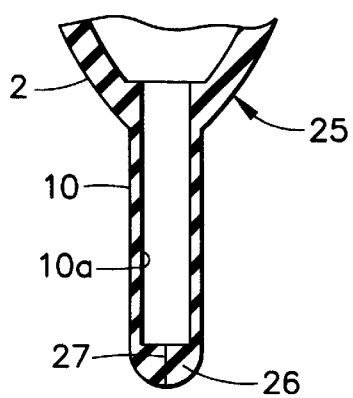
FIG. 9 is a fragmentary cross sectional view illustrating a tubular extension having a rounded closed free end provided with a slit.

The embodiment 25 of FIG. 9 is somewhat similar to that of FIG. 6. The extension 10 is tubular, having a longitudinally extending cylindrical passage 10a. In this instance, the extension terminates in a solid rounded closed end 26. A slit 27 is formed in the rounded end 26, extending from the exterior thereof to said passage 10a. The slit is normally maintained in a closed condition by the solid rounded end. If, however, the solid rounded end is grasped by the user and squeezed, the rounded end will be distorted, opening the normally closed slit 27. This will enable fluid to drain from the body 2 of the mentrual cup. Upon release of the rounded extension end, the slit will return to its normal closed condition.

The embodiments of FIGS. 2–9 are exemplary only. Any appropriate means may be used to releasably close the passage 10a of extension 10, so long as it meets the criteria set forth above.

As used herein and in the claims words such as "upper" and "lower" apply to the drawings and are used for purposes of explanation. It will be understood that the menstrual cup can have various orientations during use.

Modifications may be made in the invention without departing from the spirit of it.

What is claimed:

1. A menstrual cup, for use in the vagina comprising a body having a hollow interior, an open upper end and a lower end, said body being of circular transverse cross section throughout its length, an annular exterior rim means surrounding said body adjacent said open upper end for engaging the vagina wall to prevent bypass leakage, an elongated extension on said body projecting from said lower end thereof, said extension comprising a removal device for said menstrual cup, said extension being tubular and having a longitudinal passage therein, said lower body end having an opening providing communication between said hollow interior of said body and said extension passage, means for normally closing said extension passage, said closing means being manually manipulable to an open state for opening said extension passage, whereby said menstrual cup can be drained of fluid without removal from the vagina.

2. The menstrual cup claimed in claim 1 wherein said menstrual cup and said extension comprise an integral, one-piece structure of soft, resilient, fluid-proof material suitable for use within the body.

3. The menstrual cup claimed in clam 1 wherein said extension has an upper end at the juncture of said extension and said lower end of said body, said extension having a lower free end, a first piece of hook and loop-type tape being affixed to said extension at the upper end thereof, a second piece of hook and loop-type tape being affixed to said extension at said lower free end thereof and aligned with said first tape piece, one of said first and second tape pieces being of the hook-type and the other of said tape pieces being of the loop type, said extension being foldable upon itself to close said passage therein, and said first and second tape pieces being so located on said extension as to releasably maintain said extension in said folded condition.

4. The menstrual cup claimed in claim 1 wherein said extension has an upper end at the juncture of said extension and said lower end of said body, said extension having a lower free end, said means for closing said extension passage comprising a plug removably insertable within said passage at said free end of said extension.

5. The menstrual cup claimed in claim 1 wherein said means for closing said extension passage comprises a resilient clamp means surrounding said extension, said clamp means having two sides configured to engage and pinch said extension closing said passage therein, said clamp having ends manually shiftable toward each other to bulge said clamp sides away from each other and open said extension passage.

6. The menstrual cup claimed in claim 1 wherein said extension has an upper end at the juncture of said extension and said lower end of said body, said extension having a lower free end, said longitudinal passage in said extension terminating short of said free end, said free end of said extension being closed, said closed free end having a normally closed slit formed therein and communicating with said passage, said free end of said extension being manually distortable to open said slit whereby to permit drainage of fluid from said menstrual cup through said extension passage and slit.

7. The menstrual cup claimed in claim 1 wherein said means for closing said extension passage comprises a planar closure member of resilient material and having top and bottom surfaces, longitudinal sides and ends, said top and bottom surfaces forming edges with said sides and ends, said edges being rounded, said closure member having a central perforation extending through its top and bottom surfaces, said perforation being elongated in a direction parallel to said sides; said closure member being mounted on said menstrual cup extension, said extension passing through said perforation in said closure member, said closure member perforation having a length and a width such that said menstrual cup extension passing therethrough is flattened therein and said extension passage is closed, said ends of said resilient closure member being manually shiftable toward each other widening said closure member perforation and opening said extension passage.

8. The menstrual cup claimed in claim 2 wherein said menstrual cup and extension are molded of food grade gum rubber.

9. The menstrual cup claimed in claim 4 including a filament, said filament having a first end attached to said free end of said extension, said filament having a second end attached to said plug, said plug being captive with respect to said menstrual cup.

10. The menstrual cup claimed in claim 5 wherein said clamp is adhesively affixed to said extension.

11. The menstrual cup claimed in claim 6 wherein said closed free end of said extension is flattened.

12. The menstrual cup claimed in claim 6 wherein said closed free end of said extension is rounded.

13. The menstrual cup claimed in claim 7 wherein said closure member has a peripheral configuration from the class consisting of oval and obround.

14. The menstrual cup claimed in claim 7 wherein said closure member is adhesively affixed to said extension.

* * * * *